United States Patent
Jones et al.

[11] Patent Number: 6,046,347
[45] Date of Patent: Apr. 4, 2000

[54] ALUMINOXANE SYNTHESIS EMPLOYING REDUCED AMOUNT OF TRIALKYLALUMINUM COMPOUND

[75] Inventors: Paul D. Jones, State College, Pa.;
Dennis B. Malpass, LaPorte, Tex.;
Elliot I. Band, Pleasantville, N.Y.;
Gregory M. Smith, Danbury, Conn.;
Barbara L. Simms Hudock, Clinton Corners, N.Y.

[73] Assignee: Akzo Nobel nv, Arnhem, Netherlands

[21] Appl. No.: 09/160,081

[22] Filed: Sep. 24, 1998

[51] Int. Cl.$^7$ ............................................. C07F 5/06
[52] U.S. Cl. ........................ 556/179; 556/180; 556/187; 526/160; 526/943; 502/103; 502/117; 502/152
[58] Field of Search ..................... 556/179, 180, 556/187; 502/103, 117, 152; 526/160, 943

[56] References Cited

U.S. PATENT DOCUMENTS

| | | | |
|---|---|---|---|
| 4,055,634 | 10/1977 | Brenner et al. | 424/47 |
| 5,157,008 | 10/1992 | Sangokoya et al. | 502/111 |
| 5,728,855 | 3/1998 | Smith et al. | 556/179 |
| 5,777,143 | 7/1998 | Malpass et al. | 556/179 |

FOREIGN PATENT DOCUMENTS

| | | |
|---|---|---|
| 348126 | 12/1989 | European Pat. Off. . |
| 368644 | 5/1990 | European Pat. Off. . |
| 372617 | 6/1990 | European Pat. Off. . |

OTHER PUBLICATIONS

Comprehensive Organometallic Chemistry II, E.W. Abel et al., eds., Pergamon, Elsevier Science Inc., Tarrytown, NY, 1995, vol. 1, pp. 452 and 498–499.

S. Pasynkiewicz, "Alumoxanes: Synthesis, Structures, Complexes and Reactions", Polyhedron, vol. 9, No. 2/3, pp. 429–453 (1990).

S. Pasynkiewicz, "Some Reactions of Alumoxanes", Macromol. Symp. 97, 1–13 (1995).

*Primary Examiner*—Porfirio Nazario-Gonzalez
*Attorney, Agent, or Firm*—Richard P. Fennelly

[57] ABSTRACT

A catalytically active aluminoxane can be synthesized from a precursor formed by the combination of at least one trialkylaluminum compound and at least one organoaluminum compound containing a carbon-oxygen bond therein, such as an alkoxy group-containing organoaluminum compound of the formula $(CH_3)_2Al-O-R$, where R is alkyl.

9 Claims, No Drawings

ALUMINOXANE SYNTHESIS EMPLOYING REDUCED AMOUNT OF TRIALKYLALUMINUM COMPOUND

BACKGROUND OF THE INVENTION

It is well known in the art to synthesize aluminoxane compositions, which have utility as co-catalyst components, utilizing at least one trialkylaluminum compound as a reagent. It is further well known to synthesize these aluminoxane compositions by reacting the trialkylaluminum reagent(s) with a water source. More recently, as described in U.S. Pat. No. 5,831,109 or in U.S. Pat. No. 5,777,143 (which are incorporated herein in their entirety for their disclosures), methods using a compound containing a carbon-oxygen bond, such as carbon dioxide, to form a precursor composition that can be converted to the desired aluminoxane product have been disclosed. It is obvious to a person skilled in the art that these methods could also be combined. For instance, a precursor formed using a carbon-oxygen bond containing reagent could be partially hydrolyzed, and then finally converted to an aluminoxane composition. Alternatively, hydrolysis could be conducted prior to reaction with a carbon-oxygen bond containing reagent.

It is also known in the art to synthesize aluminoxane compositions, which have utility as co-catalyst components, by utilizing at least one trialkylaluminum compound as a reagent which is treated with a reagent containing a carbon-oxygen double bond, such as carbon dioxide, and water, as described in U.S. Pat. No. 5,728,855 (incorporated herein in its entirety for its disclosures).

In the foregoing preparative schemes, the aluminum in the aluminoxane is substantially derived from the trialkylaluminum compound, which is commonly trimethylaluminum. This trialkylaluminum reagent is generally the most expensive component in the reagent system. If all or a portion of the trialkylaluminum compound could be replaced as the source for the aluminum in the final product, the manufacturing process could be made correspondingly less expensive.

SUMMARY OF THE INVENTION

This invention is directed to a less costly aluminoxane manufacturing procedure in which all or a portion of the trialkylaluminum compound is replaced as the source for the aluminum in the final aluminoxane product by a less costly aluminum-containing reagent. The present invention is a process for the synthesis of an aluminoxane which comprises conversion of a precursor formed by the combination of at least one trialkylaluminum compound and, as the generally less costly reagent, at least one organoaluminum compound containing a carbon-oxygen bond therein. Conversion of the precursor to an aluminoxane can comprise exclusively nonhydrolytic processes, hydrolysis with water, or a combination of hydrolysis and nonhydrolytic processes.

DESCRIPTION OF THE PREFERRED EMBODIMENTS

The present invention relies upon the replacement of all or a portion of the trialkylaluminum reagent conventionally used as the aluminum source in synthesis of a cocatalytically active aluminoxane (regardless of process). The cocatalytically active aluminoxane may be useful in a number of processes, including but not limited to Zieger-Natta olefin polymerization, metallocene catalyzed olefin polymerization, polymerization using single-site catalysts, or other polymerization processes using molecular catalysts that are activated by aluminoxanes. The replacement is made by an organoaluminum compound containing a carbon-oxygen bond therein and may be illustrated by the following set of reactions (R for instance being methyl and R' being another alkyl group, such as one containing from about 4 to about 10 carbon atoms):

$$0.8R_2Al\text{—}OR'+0.2R_3Al \rightarrow R_{2.2}Al(OR')_{0.8}$$

The foregoing reaction can be carried out at room temperature in a suitable hydrocarbon solvent. Examples of suitable solvents include, but are not limited to, aromatic solvents such as benzene, toluene, xylene and cumene, or linear or branched aliphatic solvents such as butane, pentane, isopentane, hexane, heptane, etc. Many compounds other than $R_2Al$—$OR'$ can also be employed, if desired. For instance:

$$0.4RAl(OR')_2+0.6R_3Al \rightarrow R_{2.2}Al(OR')_{0.8}$$

$$0.4R_2Al(O_2CR')+0.6R_3Al \rightarrow R_{1.8}AlO_{0.4} \ (OCR' \ R_2)_{0.4}$$

Workers skilled in the art could easily envision additional examples. The $R_2AlOR'$ compound, or similar effective compounds, may be prepared by any number of means know to persons skilled in the art. As a trivial example, it could be formed by reaction of dimethylaluminum chloride with an alkali metal alkoxide, such as sodium t-butoxide in accordance with the formula:

$$NaOt\text{—}Bu+Me_2AlCl \rightarrow NaCl\downarrow+Me_2AlOt\text{—}Bu$$

Then, the product of the foregoing reaction where part or all the trialkylaluminum reagent is replaced by an organoaluminum compound containing a carbon-oxygen bond therein can be converted to an aluminoxane product. The conversion could be simple hydrolysis as described in U.S. Pat. No. 5,728,855, or it could be a nonhydrolytic process as described, for instance, in U.S. Pat. No. 5,831,109 or in U.S. Pat. No. 5,777,143. The conversion could also be a combination of the foregoing, such as hydrolysis followed by nonhydrolytic conversion to aluminoxane.

One example of nonhydrolytic conversion of that precursor composition into an aluminoxane product, as further described in U.S. Pat. No. 5,831,109 or in U.S. Pat. No. 5,777,143, would be:

$$R_{2.2}Al(OR')_{0.8} \rightarrow R_{1.4}Al(O)_{0.8}+\text{Organic By-Products}$$

It is well within the skill in the art to vary the stoichiometries depicted above, which are presented for illustrative purposes only, to employ a combination of water and thermal conversion techniques with the precursor which is formed, and to employ other C—O containing compounds (as further described in U.S. Pat. No. 5,831,109 or in U.S. Pat. No. 5,777,143). For example, in regard to the general types of reaction which can be used, the following additional reaction are exemplifies one alternative:

$$0.4R_2Al\text{—}OR'+0.6R_3Al \rightarrow R_{2.6}Al(OR')_{0.4}$$

$$R_{2.6}Al(OR')_{0.4}+0.4H_2O \rightarrow R_{1.4}Al(O)_{0.8}+\text{Organic By-Products}$$

The conversion of the previously described precursor, where some or all of the conventionally used trialkylaluminum compound is replaced, into the desired aluminoxane product takes place more quickly (e.g., about fourteen hours versus about twenty hours) as compared to the thermolysis reaction described in U.S. patent application Ser. No. 08/576,892 or in U.S. Pat. No. 5,777,143 where only a trialkylaluminum reagent is employed as the initial reagent to supply the aluminum values to the ultimate aluminoxane product. Also, the aluminoxane produced by the process of the present invention has a proton NMR spectrum which is characteristic of conventional aluminoxane as well as the non-hydrolytically treated aluminoxane obtained from the process described and claimed in U.S. patent application Ser. No. 08/576,892 or in U.S. Pat. No. 5,777,143.

The aluminoxane formed by the process of the present invention can be used in the same applications previously taught for conventional aluminoxane compositions.

The present invention is further illustrated by the Examples that follow.

EXAMPLE 1

Dimethylaluminum tert-butoxide (DMAL-TB), 8.874 g, 44.4 mmole of Al; trimethylaluminum (TMAL), 0.801 g, 11.1 mmole of Al); polymethylaluminoxane (PMAO), 2.350 g, 11.4 of mmole Al, which is synthesized by the reaction described and claimed in U.S. patent application Ser. No. 08/576,892; tri-n-octylaluminum (TNOAL), 0.410 g, 1.12 mmole of Al); and toluene, 2.882 g, were combined in a three neck, 250 mL round bottom. This was thermolyzed at a bulk temperature of 105° C. for thirteen and one-half hours. The progress of the reaction was followed by proton nuclear magnetic resonance ($^1$H NMR). The result was a clear, viscous fluid that was active as a co-catalyst in ethylene polymerization.

EXAMPLE 2

In this Example, DMAL-TB (15.338 g, 76.8 mmole of Al), TMAL (1.385 g, 19.2 of mmole Al), $CO_2$-treated TMAL (8.997, 38.4 mmole of Al), TNOAL (0.700 g, 1.92 mmole of Al) and toluene (4.585 g) were placed in a three neck, 250 mL round bottom flask. This was thermolyzed at a bulk temperature of 105° C. The product was a clear, viscous liquid that functioned as an active co-catalyst in an ethylene polymerization.

The preceding Examples, since they are only intended to illustrate certain embodiments of the invention, should not be construed in a limiting sense. The scope of protection sought is set forth in the claims that follow.

We claim:

1. A process for the synthesis of an aluminoxane which comprises conversion of a precursor formed by the combination of at least one trialkylaluminum compound and at least one organoaluminum compound containing a carbon-oxygen bond therein to form a catalytically active aluminoxane.

2. A process as claimed in claim 1 wherein the conversion to the catalytically active aluminoxane is accomplished by thermolysis.

3. A process for the synthesis of an aluminoxane which comprises conversion of a precursor formed by the combination of at least one trialkylaluminum and at least one organoaluminum compound containing a carbon-oxygen bond therein to form a catalytically active aluminoxane, wherein the conversion of the precursor is accomplished by a combination of hydrolysis and thermolysis.

4. A process as claimed in claim 1 wherein the conversion to the catalytically active aluminoxane is accomplished by hydrolysis.

5. A process as claimed in any of claims 1–4 wherein the trialkylaluminum compound is trimethylaluminum.

6. A process as claimed in any of claims 1–4 wherein the trialkylaluminum compound is trimethylaluminum and the alkoxy group-containing organoaluminum compound is of the formula $(Ch_3)_2Al$—O—R, where R is alkyl.

7. A process as claimed in any of claims 1–4 wherein the trialkylaluminum compound is trimethylaluminum and the alkoxy group-containing organoaluminum compound is of the formula $(CH_3)_2Al$—O—R, where R is alkyl containing up to about 10 carbon atoms.

8. A process as claimed in any of claims 1–4 wherein the trialkylaluminum compound is trimethylaluminum and the alkoxy group-containing organoaluminum compound is of the formula $(CH_3)_2Al$—O—R, where R is t-butyl.

9. A process for the synthesis of an aluminoxane which comprises conversion of a precursor, formed by the combination of a) the product from reaction of at least one trialkylaluminum compound with at least one organic compound containing a carbon-oxygen bond and b) at least one organoaluminum compound containing a carbon-oxygen bond therein to form a catalytically active aluminoxane.

* * * * *